(12) United States Patent
Mitsuno et al.

(10) Patent No.: US 9,044,360 B2
(45) Date of Patent: Jun. 2, 2015

(54) NONWOVEN FABRIC, ABSORBENT ARTICLE COMPRISING THE SAME, AND METHOD OF FORMING THE SAME

(75) Inventors: Satoshi Mitsuno, Kagawa (JP); Masashi Nakashita, Kagawa (JP)

(73) Assignee: Unicharm Corporation, Ehime (JP)

( * ) Notice: Subject to any disclaimer, the term of this patent is extended or adjusted under 35 U.S.C. 154(b) by 129 days.

(21) Appl. No.: 13/812,491

(22) PCT Filed: Sep. 22, 2011

(86) PCT No.: PCT/JP2011/072498
§ 371 (c)(1),
(2), (4) Date: Jan. 25, 2013

(87) PCT Pub. No.: WO2012/043779
PCT Pub. Date: Apr. 5, 2012

(65) Prior Publication Data
US 2013/0172842 A1    Jul. 4, 2013

(30) Foreign Application Priority Data

Sep. 27, 2010   (JP) .................................. 2010-215675

(51) Int. Cl.
| | |
|---|---|
| A61F 13/15 | (2006.01) |
| D04H 5/00 | (2012.01) |
| D02G 3/00 | (2006.01) |
| D04H 3/16 | (2006.01) |
| D04H 3/08 | (2006.01) |
| A61F 13/539 | (2006.01) |
| D04H 1/4382 | (2012.01) |
| D04H 1/4391 | (2012.01) |
| D04H 1/541 | (2012.01) |
| A61F 13/511 | (2006.01) |
| D04H 1/492 | (2012.01) |
| D04H 1/558 | (2012.01) |

(52) U.S. Cl.
CPC ............ *A61F 13/539* (2013.01); *D04H 1/4382* (2013.01); *D04H 1/4391* (2013.01); *D04H 1/541* (2013.01); *A61F 13/511* (2013.01); *A61F 13/15617* (2013.01); *D04H 1/492* (2013.01); *D04H 1/558* (2013.01)

(58) Field of Classification Search
USPC .......... 604/378, 365, 384, 370; 442/327, 361, 442/362, 363, 364; 428/373, 374; 156/181, 156/167
See application file for complete search history.

(56) References Cited

U.S. PATENT DOCUMENTS 4,547,420 A * 10/1985 Krueger et al. ............... 442/347

FOREIGN PATENT DOCUMENTS

| CN | 1681986 A | 10/2005 |
|---|---|---|
| JP | 2003-89955 A | 3/2003 |

(Continued)

OTHER PUBLICATIONS

International Search Report from corresponding PCT application No. PCT/JP2011/072498 dated Dec. 13, 2011 (2 pgs).

*Primary Examiner* — Jacqueline Stephens
(74) *Attorney, Agent, or Firm* — Brinks Gilson & Lione

(57) ABSTRACT

A nonwoven fabric with excellent feel on the skin, excellent air permeability and liquid permeability, and high deformability and superior recoverability. The nonwoven fabric comprises composite fibers that include a first component, and a second component having a lower melting point than the first component, wherein detached portions are created by detaching at least a portion of the second component from the first component and/or the residual portion of the second component, and at least some of the detached portions are tangled and/or fused with other composite fibers.

14 Claims, 10 Drawing Sheets

(56) References Cited

FOREIGN PATENT DOCUMENTS

| | | |
|---|---|---|
| JP | 2003-089955 A | 3/2003 |
| JP | 2009-62650 A | 3/2008 |
| JP | 2011-226010 A | 11/2011 |
| WO | WO 2004/022831 A1 | 3/2004 |
| WO | WO 2005/042824 A1 | 5/2005 |

* cited by examiner (a)

(b)

(c)

(d)

(e)

(a)

(b)

(c)

100μm

666μm

NONWOVEN FABRIC, ABSORBENT ARTICLE COMPRISING THE SAME, AND METHOD OF FORMING THE SAME

RELATED APPLICATION

This application is a 35 U.S.C. §371 national phase filing of International Patent Application No. PCT/JP2011/072498, filed Sep. 22, 2011, through which and to which priority is claimed under 35 U.S.C. §119 to Japanese Patent Application No. 2010-215675, filed Sep. 27, 2010.

TECHNICAL FIELD

The present invention relates to a nonwoven fabric comprising composite fibers comprising a first component, and a second component having a lower melting point than the first component, and having a specific tangled and/or fused structure, as well as to an absorbent article comprising the nonwoven fabric and a method of forming the nonwoven fabric.

BACKGROUND ART

Nonwoven fabrics are used in absorbent articles such as sanitary products and disposable diapers, cleaning products such as wipers, and medical goods such as masks. However, the nonwoven fabrics used in such products usually have specialized functions according to the purpose of the products and their location of use.

With absorbent articles, for example, it is necessary to employ nonwoven fabrics that expand and contract in response to bodily movement during wear or use, without creating an uncomfortable feeling for the user. Disposable diapers and sanitary napkins require nonwoven fabrics with high elasticity and strength sufficient to prevent tearing during extension, as well as satisfactory feel on the skin, air permeability and liquid-permeability.

Nonwoven fabrics exhibiting the desired performance in such products are usually designed and produced for each individual product. It is therefore considered preferable, from the viewpoint of production cost and environmental protection, for nonwoven fabrics exhibiting desired performance to be more easily formed by modifying certain nonwoven fabrics such as commercially available nonwoven fabrics.

As a method of forming a nonwoven fabric suitable for use in an absorbent article comprising a nonwoven fabric as the starting material, PTL 1 discloses a nonwoven fabric having alternating ridges and furrows each extending in one direction, with openings in the furrows, wherein the ridges have a substantially greater fiber content than the furrows, and the fiber density differs between the tops of the ridges and the edges of the openings. In paragraph [0048] of PTL 1 it is stated that a nonwoven fabric with bonded and entangled fibers may be used as the starting material for the nonwoven fabric.

PTL 1 also teaches that the nonwoven fabric that is formed has excellent flexibility and low liquid retention, and that its air permeability along the furrows is excellent.

CITATION LIST

Patent Literature

PTL 1 Japanese Unexamined Patent Publication No. 2009-62650

SUMMARY OF INVENTION

Technical Problem

However, when a commercially available nonwoven fabric, for example, is used as the starting material for the invention described in PTL 1, a high level of energy is required for fluid treatment because the fibers of the nonwoven fabric are fixed and not easily moved. When water vapor or an air stream is used as fluid treatment, the fluid treatment temperature must be increased, but a higher treatment temperature results in fusion of the fibers in the nonwoven fabric and reduced flexibility of the nonwoven fabric that is produced, while also making it difficult to form the desired structure. As a result, the nonwoven fabric described in PTL 1 has a structure with a low degree of freedom of the fibers and resistance to deformation against external force, and can sometimes hurt the skin when it is used in sections that directly contact the skin and are subjected to body pressure. Furthermore, since the nonwoven fabric described in PTL 1 has compacted fibers, it tends to retain liquids and presumably has low liquid-permeability.

It is therefore an object of the present invention to provide a nonwoven fabric with excellent feel on the skin, excellent air permeability and liquid permeability, and also high deformability and superior recoverability.

Solution to Problem

As a result of diligent research directed toward solving the problems described above, the present inventors have found that the aforementioned problems can be solved by a nonwoven fabric comprising composite fibers that include a first component, and a second component having a lower melting point than the first component, wherein detached portions are created by detaching at least a portion of the second component from the first component and/or residual portions of the second component, at least some of the detached portions being tangled and/or fused with other composite fibers.

Specifically, the present invention relates to the following aspects.

[Aspect 1]

A nonwoven fabric comprising composite fibers that include a first component, and a second component having a lower melting point than the first component, wherein detached portions are created by detaching at least a portion of the second component from the first component and/or residual portions of the second component, and at least some of the detached portions are tangled and/or fused with other composite fibers.

[Aspect 2]

The nonwoven fabric according to aspect 1, wherein the detached portions are formed by detaching at least a portion of the second component from the first component and/or the residual portions of the second component along roughly the longitudinal axial direction of the composite fibers.

[Aspect 3]

The nonwoven fabric according to aspect 1 or 2, wherein the composite fibers are selected from the group consisting of core-sheath composite fibers, sea-island composite fibers, split mold composite fibers, side-by-side composite fibers and mixtures thereof.

[Aspect 4]

The nonwoven fabric according to any one of aspects 1 to 3, wherein the composite fibers are core-sheath composite fibers in which the first component is the core and the second component is the sheath, and a portion of the core is exposed without being covered by the sheath.

[Aspect 5]

The nonwoven fabric according to any one of aspects 1 to 4, wherein the nonwoven fabric has a first side with a plurality of projections and a plurality of recesses, and a second side on the opposite side from the first side, with a plurality of projections and a recess.

[Aspect 6]

The nonwoven fabric according to aspect 5, wherein the diameter of the composite fibers in the projections of the second side is smaller than the diameter of the composite fibers in the recesses on the second side.

[Aspect 7]

The nonwoven fabric according to aspect 5 or 6, wherein the percentage of the detached portion among the projections on the second side is higher than the percentage of the detached portion among the recesses on the second side.

[Aspect 8]

The nonwoven fabric according to any one of aspects 1 to 7, wherein the first component has a melting point of at least 20° C. higher than the second component.

[Aspect 9]

The nonwoven fabric according to any one of aspects 1 to 8, wherein the nonwoven fabric is formed by non-homogeneous stretching an air-through nonwoven fabric comprising composite fibers comprising the first component, and the second component having a lower melting point than the first component, so that a nonwoven fabric with high-stretch regions and low-stretch regions is formed, followed by spraying a fluid onto the nonwoven fabric with high-stretch regions and low-stretch regions.

[Aspect 10]

An absorbent article comprising a liquid-permeable top sheet, a liquid-impermeable back sheet and an absorbent core between the liquid-permeable top sheet and liquid-impermeable back sheet, wherein the liquid-permeable top sheet is a nonwoven fabric according to any one of aspects 1 to 9.

[Aspect 11]

A method of forming the nonwoven fabric according to any one of aspects 1 to 9, the method comprising the steps of, providing a nonwoven fabric comprising composite fibers comprising a first component, and a second component having a lower melting point than the first component, non-homogeneous stretching of the nonwoven fabric comprising the composite fibers comprising the first component and the second component having a lower melting point than the first component, so that detached portions are created by detaching at least a portion of the second component from the first component and/or residual portions of the second component, to form a nonwoven fabric with high-stretch regions and low-stretch regions, and spraying a fluid onto the nonwoven fabric with high-stretch regions and low-stretch regions so that at least some of the detached portions become tangled and/or fused with other composite fibers, to form the nonwoven fabric according to any one of aspects 1 to 9.

[Aspect 12]

The method according to aspect 11, wherein in the step of spraying the fluid, a support having protrusions and depressions with predetermined shapes and arrangements is placed on the side opposite the fluid-sprayed side of the nonwoven fabric with high-stretch regions and low-stretch regions.

[Aspect 13]

The method according to aspect 11 or 12, wherein the fluid is heated air, saturated steam or superheated steam.

[Aspect 14]

The method according to any one of aspects 11 to 13, wherein the nonwoven fabric comprising composite fibers comprising the first component and the second component having a lower melting point than the first component are of an air-through nonwoven fabric.

Advantageous Effects of Invention

In the nonwoven fabric of the invention, detached portions are formed by detaching at least a portion of the second component from the first component and/or residual portions of the second component, and at least some of the detached portions are tangled and/or fused with other composite fibers, and therefore the degree of freedom between composite fibers is high, while the fabric is flexible and has excellent feel on the skin, excellent air permeability and liquid permeability and high deformability and superior recoverability.

DESCRIPTION OF EMBODIMENTS

The nonwoven fabric of the invention, an absorbent article comprising the nonwoven fabric, and the method of forming a nonwoven fabric, will now be explained in detail.

[Nonwoven Fabric of the Invention]

The nonwoven fabric of the invention is a nonwoven fabric comprising composite fibers that include a first component and a second component having a lower melting point than the first component. In the nonwoven fabric of the invention, detached portions are formed by detaching at least a portion of the second component from the first component and/or residual portions of the second component, and at least some of the detached portions are tangled and/or fused with other composite fibers (hereunder also referred to as "specific tangled and/or fused structure").

As used herein, the term "tangled" refers to a state in which at least some of the detached portions of the second component are twined around other composite fibers, and the term "fused" refers to a state in which at least some of the detached portions of the second component in that section are anchored with other composite fibers.

The extent of the twined state for exhibiting the effect of the invention is preferably such that the detached portion is twined at least ¼ turn, more preferably twined at least ½ turn and even more preferably twined at least 1 full turn around the other composite fibers, in the direction perpendicular to the lengthwise direction of the fibers.

Figure 1:
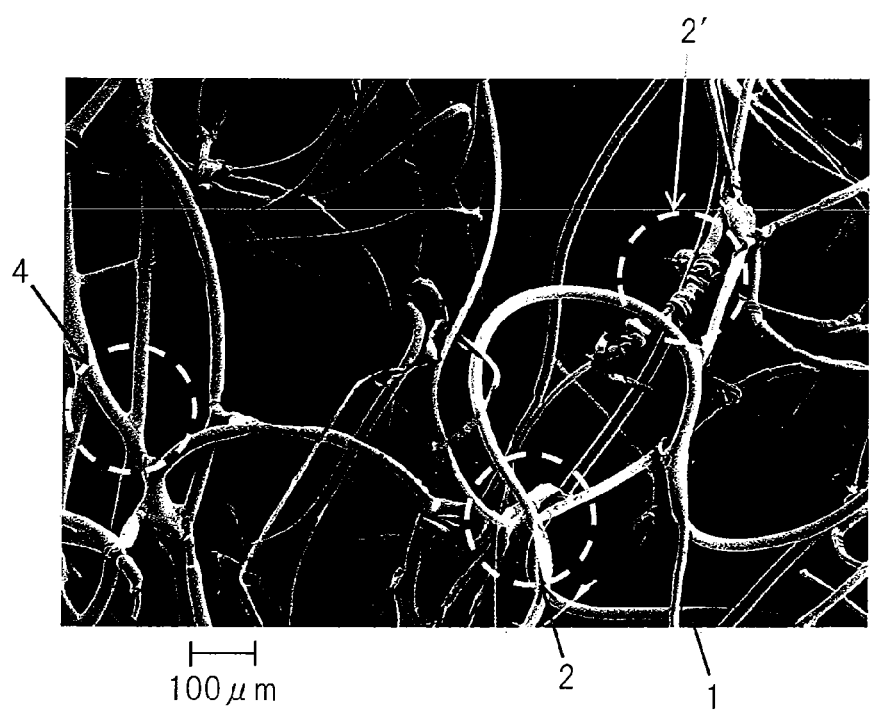
FIG. 1 is a scanning electron micrograph of an embodiment of a nonwoven fabric of the invention.
Figure 2:
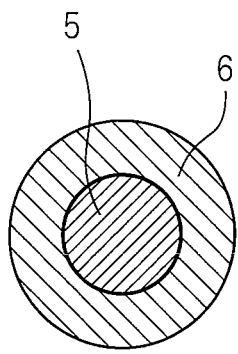
FIGS. 2(a)-(e) are diagrams showing examples of cross-sections of composite fibers to be used in the nonwoven fabric of the invention.
Figure 2:
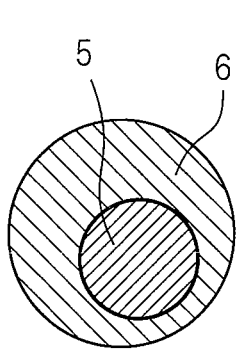
Figure 2:
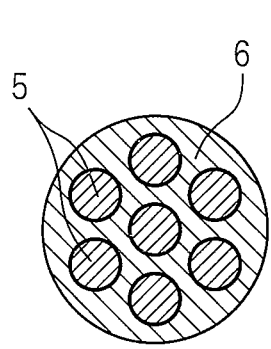
Figure 2:
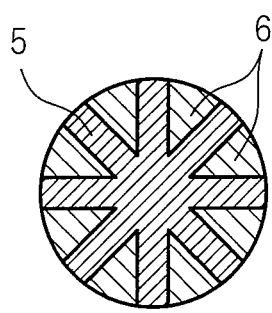
Figure 2:
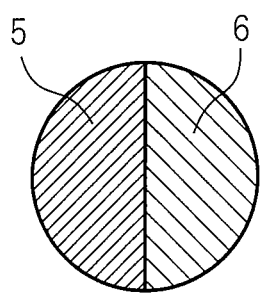

FIG. 1 is a scanning electron micrograph of an embodiment of a nonwoven fabric of the invention. The nonwoven fabric shown in FIG. 1 comprises composite fibers 1 as the core-sheath composite fibers and a detached portion 2 tangled and/or fused with other composite fibers. In the nonwoven fabric shown in FIG. 1, in addition to the detached portion 2 tangled and/or fused with other composite fibers there are observed a detached portion 2' not tangled and/or fused with the other composite fibers, and a joining section 4 between composite fibers.

As used herein, the term "joining section" refers to a section where the fibers are fused together without forming a detached portion.

FIG. 1 is an electron micrograph of the surface of the nonwoven fabric 2 produced in Example 2.

In the detached portion 2 tangled and/or fused with other composite fibers, a detached portion is formed by detaching the sheath of the composite fibers from the core, and it is tangled and/or fused with another composite fiber. Also, in the detached portion 2 tangled and/or fused with other composite fibers, the sheath and core of the composite fiber are independent, with the sheath behaving as if it were itself a fiber, being loosely tangled and/or fused with another composite fiber. Thus, each composite fiber is not easily anchored, and the composite fibers are therefore connected together while maintaining the degree of freedom of the composite fibers.

In the detached portion 2' which is not tangled and/or fused with other composite fibers, the sheath of the composite fiber is detached from the core so that a detached portion is formed, but the detached portion is not tangled and/or fused with another composite fiber.

In the joining section 4 between composite fibers, two composite fibers are fused together without the sheaths of the composite fibers being detached from the cores. Also, in the joining section 4 between the composite fibers, the shapes of the composite fibers are maintained without significant deformation of the shapes of the composite fibers.

The joining section 4 between composite fibers in FIG. 1 is a heat-fused section present in the air-through nonwoven fabric before the non-homogeneous stretching step has been carried out.

The composite fibers used in the nonwoven fabric of the invention may be of any type without any particular restrictions so long as they comprise at least two components, namely a first component and a second component having a lower melting point than the first component, with at least two regions of the first component and second component in a cross-section of the composite fiber wherein at least a portion of the region consisting of the second component is present on the fiber surface, and examples include core-sheath composite fibers, sea-island composite fibers, split mold composite fibers and side-by-side composite fibers.

The core-sheath composite fibers may be simple core composite fibers, such as concentric circular or eccentric core-sheath composite fibers.

FIGS. 2(a)-(e) show examples of cross-sections of composite fibers to be used in the nonwoven fabric of the invention. FIGS. 2(a)-(e) each show composite fibers comprising two components, a first component 5 and a second component 6, wherein FIGS. 2 (a), (b), (c), (d) and (e) show a concentric circular core-sheath composite fiber, eccentric core-sheath composite fiber, sea-island composite fiber, split mold composite fiber and side-by-side composite fiber, respectively.

There are no particular restrictions on the first component, and it may be polyethylene terephthalate, nylon, polyurethane, polyamide or a combination thereof, for example. There are also no particular restrictions on the second component so long as it is a component having a lower melting point than the first component, and it may be polyethylene, polypropylene, polyester, or a combination thereof, for example.

If the melting point of the second component is lower than the melting point of the first component, the strength of the second component will be lower than the strength of the first component, such that the second component will tend to detach more easily during the non-homogeneous stretching described below. This is because, during production, the composite fibers are spun at a temperature near the melting point of the component having the higher melting point, i.e. the first component, and therefore the component having the lower melting point, i.e. the second component is spun at a higher temperature than its melting point and has as a result a lower degree of orientation and crystallinity than the first component, and hence tends to have lower strength and greater tendency to elongation.

If the melting point of the second component is lower than the melting point of the first component, the detached portion of the second component will also be able to tangle and/or fuse with other composite fibers in the fluid treatment step described hereunder.

The difference in melting points of the first component and second component is preferably about 20° C. or more, more preferably about 40° C. or more, and even more preferably about 60° C. or more. This will increase the difference between the orientation and crystallinity of the second component and the orientation and crystallinity of the first component, and will tend to more readily form a nonwoven fabric according to the invention.

As used herein, the term "melting point" refers to the peak top temperature for the endothermic peak during conversion from solid to liquid, upon measurement with a differential scanning calorimetry analyzer at a temperature-elevating rate of 10° C./min.

FIGS. 2(a)-(e) show examples of composite fibers composed of a first component and a second component, but the composite fibers used for the invention may instead be composed of 3 or more components. If the composite fibers are composed of 3 components, a third component can be polyethylene terephthalate, nylon, polyurethane, polyamide, polyethylene, polypropylene, polyester or a combination thereof, however the third component should be different from the first and second components.

There are no particular restrictions on the sizes of the composite fibers, but when used for the top sheet of an absorbent article, they are preferably in the range from about 1 to about 6 dtex. If the sizes are less than about 1 dtex the strength of the composite fibers will be reduced, and the thickness of the nonwoven fabric will thus be reduced and the air permeability and liquid permeability of the nonwoven fabric will tend to be lower. If the sizes exceed about 6 dtex, the strength of the composite fibers themselves will increase and the feel will tend to be reduced.

Figure 3:
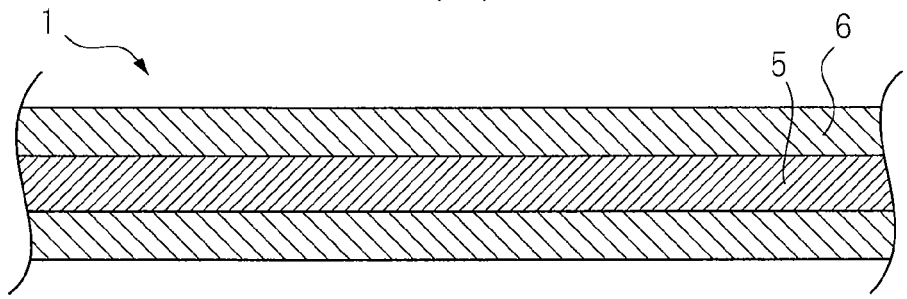
FIGS. 3(a)-(c) are diagrams illustrating a detached portion tangled and/or fused with another composite fiber, with an example of its formation.
Figure 3:
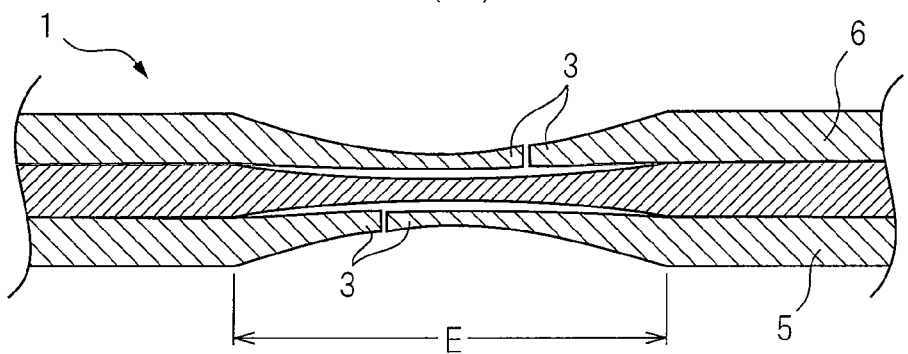
Figure 3:
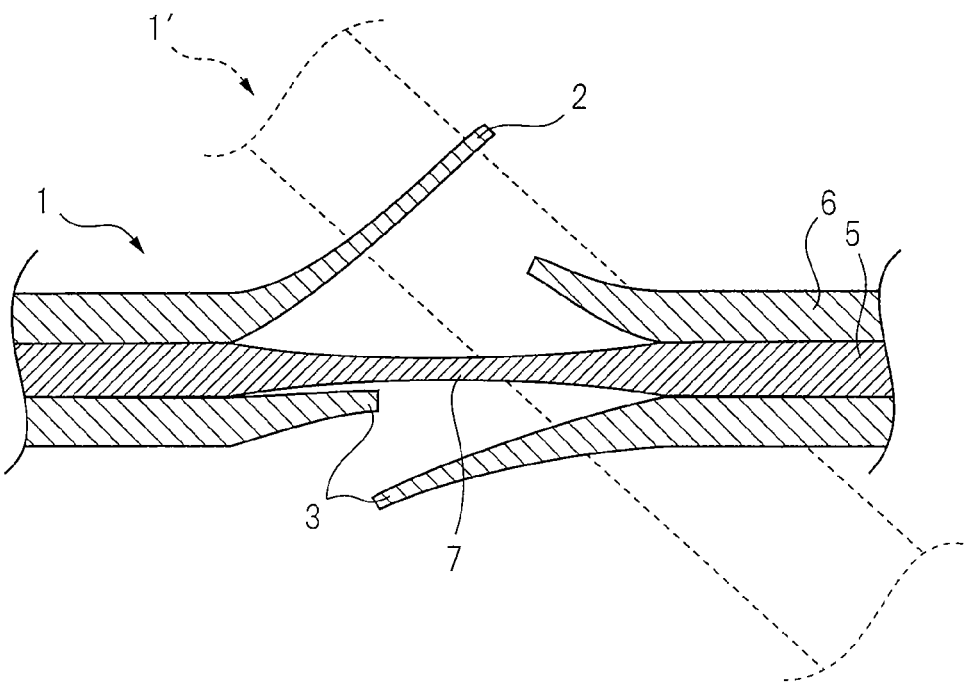

FIGS. 3(a)-(c) are diagrams illustrating a detached portion tangled and/or fused with other composite fiber, with an example of its formation. FIGS. 3(a)-(c) show cross-sections in the lengthwise direction of the composite fibers. FIG. 3(a) shows an example of the composite fiber in a nonwoven fabric before the non-homogeneous stretching step, FIG. 3(b) shows an example of the composite fiber in a nonwoven fabric after the non-homogeneous stretching step, and FIG. 3(c) shows an example of the composite fiber in a nonwoven fabric after the fluid treatment step, i.e., a nonwoven fabric of the invention.

As shown in FIG. 3(a), the composite fiber 1 is a core-sheath composite fiber having a first component 5 as the core and second component 6 as the sheath. When the non-homogeneous stretching step is carried out, as shown in FIG. 3(b), the first component 5 and the second component 6 are extended particularly in the high-stretch region E (the high-stretch region will be explained hereunder), with the second component 6 being detached from the first component 5, while at least a portion of the second component 6 with weak strength forms a detached portion 3 by being detached from the first component 5 and/or the residual portion of the second component 6.

Next, as shown in FIG. 3(c), carrying out the fluid treatment step causes at least part of the detached portion 3 to become tangled and/or fused with another composite fiber 1', forming a detached portion 2 tangled and/or fused with other composite fiber. Also, the composite fiber 1 shown in FIG. 3(c) has an exposed portion 7 wherein part of the first component 5 is not covered by the second component 6 of the sheath.

In FIG. 3(c), the other composite fiber 1' is represented by a dotted line.

The illustrations in FIGS. 3(a)-(c) are simplified for easier understanding, showing only that the detached portion 3 is formed by detaching at least a portion of the second component 6 from the first component 5. In actuality, however, the detached portion may be formed by detaching at least a portion of the second component 6 from the residual portion of the second component 6.

In the nonwoven fabric of the invention, the amount in which at least some of the detached portions are tangled and/or fused with other composite fibers may vary depending on the desired performance of the nonwoven fabric of the invention, and for example, it may be an amount such that a nonwoven fabric comprising composite fibers comprising a first component and a second component having a lower melting point than the first component is formed by subjecting an air-through nonwoven fabric, for example, to non-homogeneous stretching so as to form a nonwoven fabric having high-stretch regions and low-stretch regions, and a fluid is sprayed onto the nonwoven fabric having high-stretch regions and low-stretch regions, and the amount may be adjusted by modifying the non-homogeneous stretching step and fluid treatment step.

When the nonwoven fabric of the invention is to be used as a liquid-permeable top sheet in an absorbent article, the nonwoven fabric of the invention may be hydrophilic. This will allow contacted hydrophilic excreted fluid (urine, sweat, stool, etc.) to pass through the interior of the absorbent article more easily without remaining on the surface of the nonwoven fabric.

To obtain a nonwoven fabric of the invention having hydrophilicity, for example, the nonwoven fabric may be treated with a hydrophilic agent, the nonwoven fabric may be produced from composite fibers incorporating a hydrophilic agent, or the nonwoven fabric may be coated with a surfactant.

The nonwoven fabric of the invention may have a first side with a plurality of projections and a plurality of recesses, and a second side on the opposite side from the first side, with a plurality of projections and a recess. In the nonwoven fabric of the invention, the diameter of the composite fibers in the projections of the second side may be smaller than the diameter of the composite fibers in the recesses on the second side. Also, the percentage of the detached portions among the projections on the second side of the nonwoven fabric of the invention may be higher than the percentage of the detached portions among the recesses on the second side. These cases will now be explained in the context of the method of forming a nonwoven fabric according to the invention.

The nonwoven fabric of the invention may further comprise monofilaments commonly used in the technical field in addition to the composite fibers, within a range that allows the effect of the invention to be exhibited. Examples of such monofilaments include natural fibers, semi-natural fibers and synthetic fibers. The monofilaments are preferably synthetic fibers. This will increase the flexibility of the nonwoven fabric of the invention. When the nonwoven fabric of the invention includes monofilaments, the percentage of the monofilaments is preferably no greater than about 30 mass %, more preferably no greater than about 20 mass % and even more preferably no greater than about 10 mass %, with respect to the total amount of fiber. Thus, when the nonwoven fabric of the invention includes monofilaments, the nonwoven fabric includes about 70 to about 100 mass %, preferably about 80 to about 100 mass %, and more preferably about 90 to about 100 mass % of the composite fibers, and about 0 to about 30 mass %, preferably about 0 to about 20 mass %, and more preferably about 0 to about 10 mass % of the monofilaments, with respect to the total amount of fiber.

When the monofilaments are monofilaments consisting of synthetic fibers, their addition creates resistance to collapsing under body pressure of the user, tending to result in satisfactory air permeability, but if the percentage of monofilaments consisting of synthetic fibers is too high, the proportion of tangled and/or fused sections derived from the detached portions will tend to decrease.

The material of the monofilaments consisting of synthetic fibers may be polyethylene, polypropylene, polyester or the like. From the viewpoint of moldability, the fibers preferably have sizes of about 1-6 dtex.

The fiber lengths of the monofilaments are not particularly restricted, and there may be mentioned staple fibers and continuous filaments, for example.

[Method of Forming Nonwoven Fabric of the Invention]

The method of forming a nonwoven fabric according to the invention comprises a step of preparing a nonwoven fabric comprising composite fibers that include a first component, and a second component having a lower melting point than the first component. The nonwoven fabric used in this step is not particularly restricted so long as it is a nonwoven fabric comprising composite fibers, and it may be, for example, an air-through nonwoven fabric, point bond nonwoven fabric or spunbond nonwoven fabric comprising composite fibers including a first component and a second component having a lower melting point than the first component, and it is preferably an air-through nonwoven fabric in consideration of ease of forming the detached portions. The composite fibers may further include a third component as a component in addition to the first component and second component.

As used herein, the nonwoven fabric prepared for this step will sometimes be referred to as "nonwoven fabric before non-homogeneous stretching".

Also as used herein, the term "air-through nonwoven fabric" refers to a nonwoven fabric obtained by passing hot air through a web comprising composite fibers to melt the second component of the composite fibers and bond them to other fibers, the term "point bond nonwoven fabric" refers to a nonwoven fabric obtained by passing a web comprising composite fibers through hot embossing rolls to form thermocompression bonded sections, and the term "spunbond nonwoven fabric" refers to a nonwoven fabric obtained by passing a continuous fiber web comprising composite fibers through hot embossing rolls to form thermocompression bonded sections.

The nonwoven fabric before non-homogeneous stretching may be a commercially available nonwoven fabric, such as a commercially available air-through nonwoven fabric, or a point bond nonwoven fabric or spunbond nonwoven fabric comprising composite fibers.

The nonwoven fabric before non-homogeneous stretching may be hydrophilic, when the nonwoven fabric formed in the method of forming a nonwoven fabric of the invention is to be used as a liquid-permeable top sheet in an absorbent article, for example. This will provide hydrophilicity to the nonwoven fabric formed by the method of forming a nonwoven fabric of the invention. The method of imparting hydrophilicity to the nonwoven fabric was described above.

The nonwoven fabric before non-homogeneous stretching may further comprise monofilaments in addition to the composite fibers, in a range that allows the effect of the invention to be exhibited. The nonwoven fabric before non-homogeneous stretching may comprise the monofilaments described above, in the percentages mentioned above.

The method of forming a nonwoven fabric of the invention comprises a step in which a nonwoven fabric comprising composite fibers that include a first component, and a second component having a lower melting point than the first component, is subjected to non-homogeneous stretching so that detached portions are formed by detaching at least a portion of the second component from the first component and/or the residual portion of the second component, thereby forming a nonwoven fabric having high-stretch regions and low-stretch regions (this will hereunder also be referred to as "non-homogeneous stretching step").

In the non-homogeneous stretching step, especially in the high-stretch regions, (i) when the composite fibers are extended and undergo plastic deformation, the interface between the first component and second component becomes detached due to the difference in the extensibility of the first component and the extensibility of the second component, so that at least a portion of the second component forms detached portions. The reason for formation of the detached portions is explained in relation to FIGS. 3(a)-(c).

In the non-homogeneous stretching step, especially in the high-stretch regions, in addition to process (i) described above the following processes can be accompanied: (ii) at least some of the joining sections between the composite fibers in the nonwoven fabric are destroyed, while the second component that contributes mainly to bonding between the composite fibers often becomes detached from the first component and/or the residual portions of the second component forming detached portions, and (iii) the joining sections between the composite fibers are simply destroyed, forming a web. The joining sections may be the heat sealing points, in the case of an air-through nonwoven fabric.

As used herein, the term "high-stretch regions" refers to regions within the nonwoven fabric that are stretched so that their degree of extension is greater than the low-stretch regions, and the term "low-stretch regions" refers to regions within the nonwoven fabric that are stretched so that their degree of extension is less than the high-stretch regions, and they include regions without extension, i.e. unstretched regions.

As used herein, the term "non-homogeneous stretching" refers to stretching of the nonwoven fabric so as to form a nonwoven fabric having high-stretch regions and low-stretch regions, or in other words, stretching of the nonwoven fabric so as to form a nonwoven fabric having different degrees of extension depending on the location.

The non-homogeneous stretching step is not particularly restricted so long as it allows formation of a nonwoven fabric with high-stretch regions and low-stretch regions, and it may be carried out by any desired means, such as passing the nonwoven fabric through the gap between a pair of gear rolls each having a rotational axis line perpendicular to the machine direction and rotating while engaging the plurality of teeth arranged around the peripheral surface of each gear roll (this will hereunder also be referred to as "gear stretching").

Figure 4:
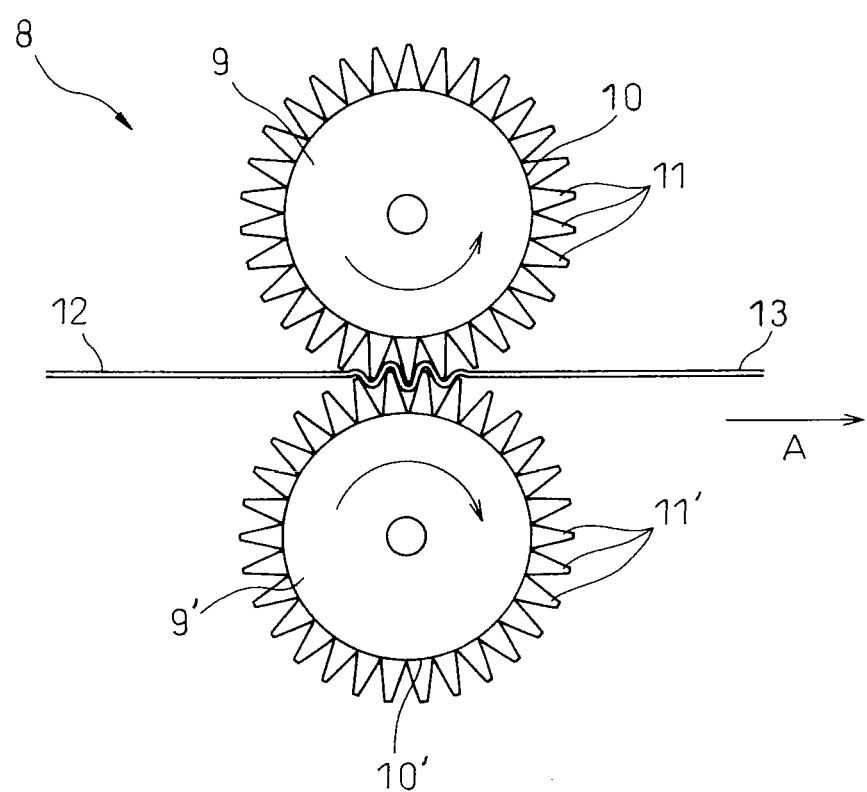
FIG. 4 is a schematic view illustrating a gear stretcher in which a plurality of teeth are arranged around the peripheral surfaces of gear rolls, parallel to the rotational axis lines of the gear rolls.

FIG. 4 is a schematic view illustrating a gear stretcher in which a plurality of teeth are arranged around the peripheral surfaces of gear rolls, parallel to the rotational axis lines of the gear rolls. The gear stretcher 8 shown in FIG. 4 has a pair of gear rolls 9 and 9'. A plurality of teeth 11 and 11' are arranged around the peripheral surfaces 10 and 10' of each of the gear rolls 9 and 9'. In the gear stretcher 8 shown in FIG. 4, the rotational axis lines of the gear rolls 9 and 9' are both perpendicular to the machine direction A. The plurality of teeth 11 and 11' are arranged parallel to the rotational axis lines of the respective peripheral surfaces 10 and 10'.

In the gear stretcher 8 shown in FIG. 4, the nonwoven fabric comprising composite fibers 12 including the first component and the second component having a lower melting point than the first component is passed through the roll gap between the pair of gear rolls 9 and 9', and when it passes through the gear rolls 9 and 9', the nonwoven fabric comprising composite fibers 12 including the first component and the second component having a lower melting point than the first component is stretched by the plurality of teeth 11 and 11' of the gear rolls 9 and 9' engaging each other, on the three-point bending principle, to form a nonwoven fabric 13 having high-stretch regions and low-stretch regions. The nonwoven fabric 13 having high-stretch regions and low-stretch regions has alternating high-stretch regions and low-stretch regions in the machine direction A, which are parallel to the direction that is perpendicular to the machine direction A (hereunder, the direction perpendicular to the machine direction will be referred to simply as the "cross direction").

In the nonwoven fabric comprising composite fibers 12 that includes the first component and the second component having a lower melting point than the first component, the fabric of the nonwoven fabric is anchored in the regions that are in contact with the tips of the plurality of teeth 11 and 11', and therefore undergoes little or no stretching, forming the low-stretch regions. On the other hand, large stretching occurs in the regions that are not in contact with the tips of the plurality of teeth 11 and 11', forming the high-stretch regions.

Figure 5:
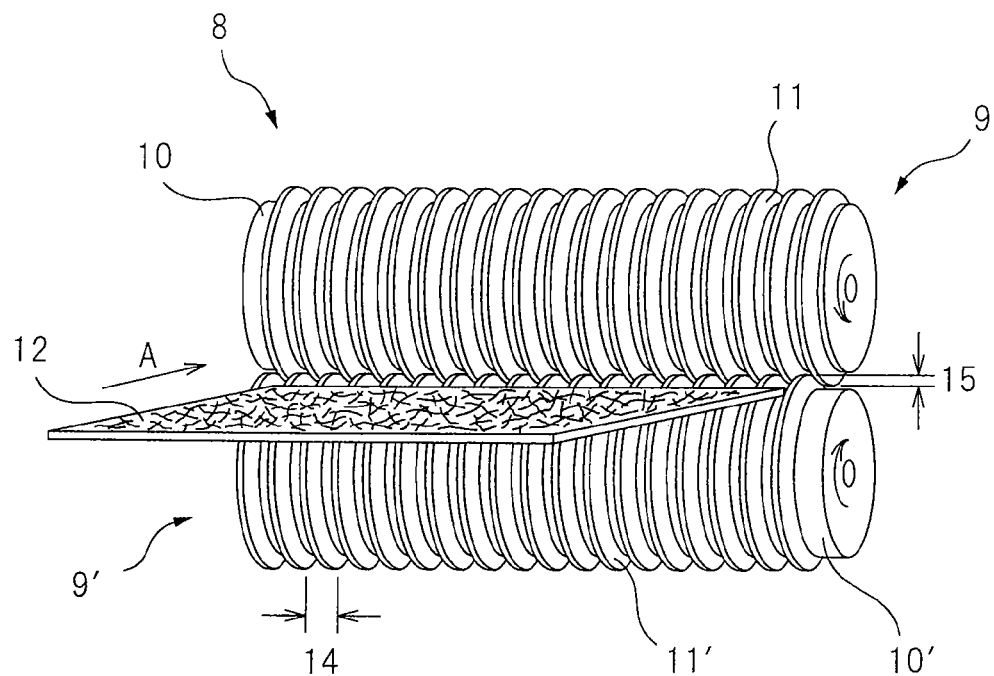
FIG. 5 is a schematic view illustrating a gear stretcher in which a plurality of teeth are arranged around the peripheral surfaces of gear rolls, perpendicular to the rotational axis lines of the gear rolls.

Gear stretching can also be accomplished using a gear stretcher as shown in FIG. 5.

FIG. 5 is a schematic view illustrating a gear stretcher in which a plurality of teeth are arranged around the peripheral surfaces of gear rolls, perpendicular to the rotational axis lines of the gear rolls. FIG. 5 is a perspective view of the gear stretcher 8, and it shows the state of the nonwoven fabric comprising composite fibers 12 that include the first component and the second component having a lower melting point than the first component, just prior to gear stretching. The nonwoven fabric comprising composite fibers 12 that include the first component and the second component having a lower melting point than the first component is gear-stretched as it proceeds from the foreground toward the background.

The gear stretcher 8 shown in FIG. 5 has a pair of gear rolls 9 and 9'. A plurality of teeth 11 and 11' are arranged around the peripheral surfaces 10 and 10' of the gear rolls 9 and 9'. In the gear stretcher 8 shown in FIG. 5, the plurality of teeth 11 and 11' are arranged on the respective peripheral surfaces 10 and 10' in a manner perpendicular to the rotational axis lines of the gear rolls 9 and 9'. When the plurality of teeth 11 and 11' are arranged in this manner, it is possible to form a nonwoven fabric having parallel high-stretch regions and low-stretch regions, parallel to the machine direction, alternating in the cross direction.

The gear stretcher may also have a plurality of teeth arranged around the peripheral surfaces of gear rolls, and slanted with respect to the rotational axis lines of the gear rolls.

Figure 6:
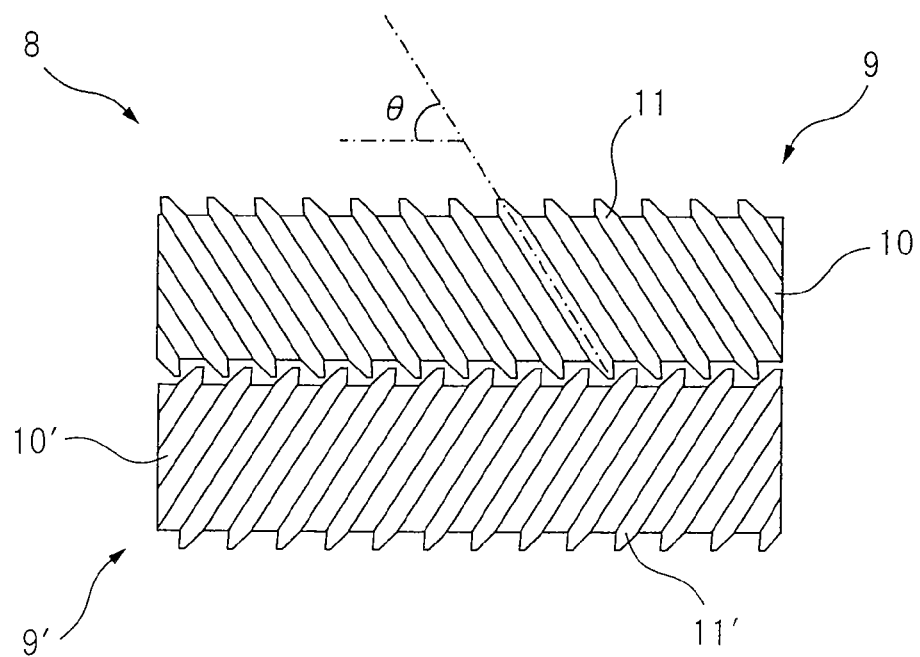
FIG. 6 is a schematic view illustrating a gear stretcher in which a plurality of teeth are arranged around the peripheral surfaces of gear rolls, slanted with respect to the rotational axis lines of the gear rolls.

FIG. 6 is a schematic view illustrating a gear stretcher in which a plurality of teeth are arranged around the peripheral surfaces of gear rolls, slanted with respect to the rotational axis lines of the gear rolls. The gear stretcher 8 shown in FIG. 6 has a pair of gear rolls 9 and 9'. A plurality of teeth 11 and 11' are arranged around the peripheral surfaces 10 and 10' of the gear rolls 9 and 9'. In the gear stretcher 8 shown in FIG. 6, the rotational axis lines of the gear rolls 9 and 9' are both perpendicular to the machine direction A. The plurality of teeth 11 and 11' are arranged around the peripheral surfaces 10 and 10' at a fixed angle of θ with respect to the rotational axis line.

The gear stretcher may be appropriately selected depending on the desired performance for the nonwoven fabric to be formed by the method of forming a nonwoven fabric of the invention.

For example, when high extensibility is required in both the machine direction and its cross direction, the nonwoven fabric before non-homogeneous stretching may employ the gear stretcher shown in FIG. 4 for stretching, and then the gear stretcher shown in FIG. 5 may be used for further stretching.

Also, the nonwoven fabric before non-homogeneous stretching may employ the gear stretcher shown in FIG. 5 for stretching, after which the gear stretcher shown in FIG. 4 may be used for further stretching.

In the gear stretchers shown in FIGS. 4 to 6, the gear pitch is preferably about 1-10 mm and more preferably about 2-6 mm. If the gear pitch is less than about 1 mm it may be necessary to reduce the thickness of the gear blades and portions of the nonwoven fabric may be severed, while if the gear pitch is greater than about 10 mm the stretch ratio may be reduced, the composite fibers may undergo plastic deformation, and detachment at the interface between the first component and second component may be insufficient.

The gear pitch is the interval between one tooth and another tooth, and it is denoted by numeral 14 in FIG. 5.

In this gear stretcher, the gear tooth cutting depth is preferably about 0.5 mm or greater. If the gear tooth cutting depth is less than about 0.5 mm, the stretch ratio may be low, the composite fibers may undergo plastic deformation, and detachment at the interface between the first component and second component may be insufficient.

The gear tooth cutting depth is the depth at the section where the top gear roll tooth and bottom gear roll tooth overlap, and it is denoted by numeral 15 in FIG. 5.

In a nonwoven fabric having high-stretch regions and low-stretch regions, the stretch ratio is preferably about 30-400% and more preferably about 50-200%. If the stretch ratio is less than about 30% the stretch ratio may be low, the composite fibers may undergo plastic deformation, and detachment at the interface between the first component and second component may be insufficient, while if the stretch ratio is greater than about 400%, the strength of the nonwoven fabric having high-stretch regions and low-stretch regions may be weak, the extended fibers may tend to shed off, and transport may be impeded.

As used herein, the term "stretch ratio" refers to the value calculated by the following formula:

$$\text{Stretch ratio } (\%) = 100 \times \left[ \frac{\sqrt{P^2 + 4D^2}}{P} - 1 \right] \quad \text{[Formula 1]}$$

where P is the gear pitch and D is the gear tooth cutting depth.

The reel-off speed of the nonwoven fabric before non-homogeneous stretching will vary depending on the desired draw ratio, but it may be about 10 m/min or greater, for example.

The method of forming a nonwoven fabric according to the invention comprises a step of spraying a fluid onto a nonwoven fabric having high-stretch regions and low-stretch regions so that at least some of the detached portions are tangled and/or fused with other composite fibers, to form a nonwoven fabric having a specific tangled and/or fused structure (hereunder also referred to as "fluid treatment step").

At least some of the detached portions in the stretched composite fibers formed in the non-homogeneous stretching step receive kinetic energy from the sprayed fluid, and become tangled with the other composite fibers.

When the temperature of the sprayed fluid is above the melting point of the second component, at least some of the detached portions melt and are fused with other composite fibers.

Depending on the type and amount of fluid that is sprayed, at least a portion of the composite fibers in the nonwoven fabric having high-stretch regions and low-stretch regions, that have been formed in the non-homogeneous stretching step, will sometimes form a first side having a plurality of projections and a plurality of recesses, as the sprayed fluid impacts the side on which the fluid impacts (hereunder referred to as "fluid-impacting side") and subsequently scatters, being sorted out in a planar direction such as the cross direction.

On the side opposite the fluid-impacting side (hereunder referred to as "non-fluid-impacting side"), at least a portion of the composite fibers in the nonwoven fabric having high-stretch regions and low-stretch regions moves along with the fluid flow, and therefore, particularly when a support having protrusions and depressions with a predetermined shape and arrangement has been provided on the side opposite the side on which the fluid is sprayed, it often forms a second side that is opposite the first side and has a plurality of projections and a recess. Such a second side will now explained below.

The fluid used in the fluid treatment step may be air, such as heated air or water vapor, such as saturated steam or superheated steam, or water such as hot water. In order to render subsequent drying either unnecessary or only minimally necessary, the fluid is preferably heated air, saturated steam or superheated steam. When the fluid is saturated steam or superheated steam, the temperature thereof is preferably about 110° C. to about 170° C.

The temperature of the fluid is not particularly restricted for "tangling" of at least some of the detached portions formed from the second component with the other composite fibers. However, for "fusion" of at least some of the detached portions formed from the second component with the other composite fibers, the temperature of the fluid is preferably at or higher than the melting point of the second component, more preferably it is at least 10° C. higher than the melting point of the second component, and even more preferably it is at least 20° C. higher than the melting point of the second component.

The temperature of the fluid is preferably lower than the melting point of the first component, more preferably at least 10° C. lower than the melting point of the first component, and even more preferably at least 20° C. lower than the melting point of the first component. This is to prevent fusion of the first component with the other composite fibers, which may harden the nonwoven fabric of the invention.

The fluid may be blasted from an anchored fluid nozzle onto the nonwoven fabric having high-stretch regions and low-stretch regions, or it may be blasted from a fluid nozzle that is reciprocating in the cross direction. The fluid may also be continuously or intermittently blasted from a fluid nozzle onto the nonwoven fabric having high-stretch regions and low-stretch regions. These may also be used in combinations.

The fluid may be appropriately selected depending on the form of the nonwoven fabric having high-stretch regions and low-stretch regions. For example, for treatment of a nonwoven fabric with a low gear pitch and a large draw ratio, a nonwoven fabric having a specific tangled and/or fused structure may be formed with relatively low energy, and therefore air or water vapor is preferably selected as the fluid. Since the joining sections between composite fibers are increased in number when using a nonwoven fabric with a large gear pitch and many low-stretch regions, a relatively high energy is necessary to form a nonwoven fabric with a specific tangled and/or fused structure, and therefore water or water vapor is preferably selected as the fluid, with water vapor being more preferred. This is because moisture does not easily remain in the sections with a large composite fiber content and the joining sections between the sections with a high composite fiber content are not usually destroyed, so that the extended composite fibers in the sections that are to undergo movement can be easily moved.

The fluid treatment step can be carried out by a known method using an apparatus known in the technical field.

According to a different embodiment of the invention, a support having protrusions and depressions (hereunder also referred to simply as "support") may be used for further improved air permeability, feel on the skin (for example, low contact area) and liquid permeability of the nonwoven fabric of the invention.

According to the invention, a "protrusion" is a section used to form a recess on the surface of the support side of the nonwoven fabric having high-stretch regions and low-stretch regions, while "depression" is a section used to form a projection on the surface of the support side of the nonwoven fabric having high-stretch regions and low-stretch regions.

A nonwoven fabric formed using a support having protrusions and depressions will have projections and recesses (and one or more open holes in some cases), and can therefore exhibit high air permeability, and especially air permeability in the planar direction, compression resistance, liquid permeability and satisfactory feel on the skin.

Figure 7:
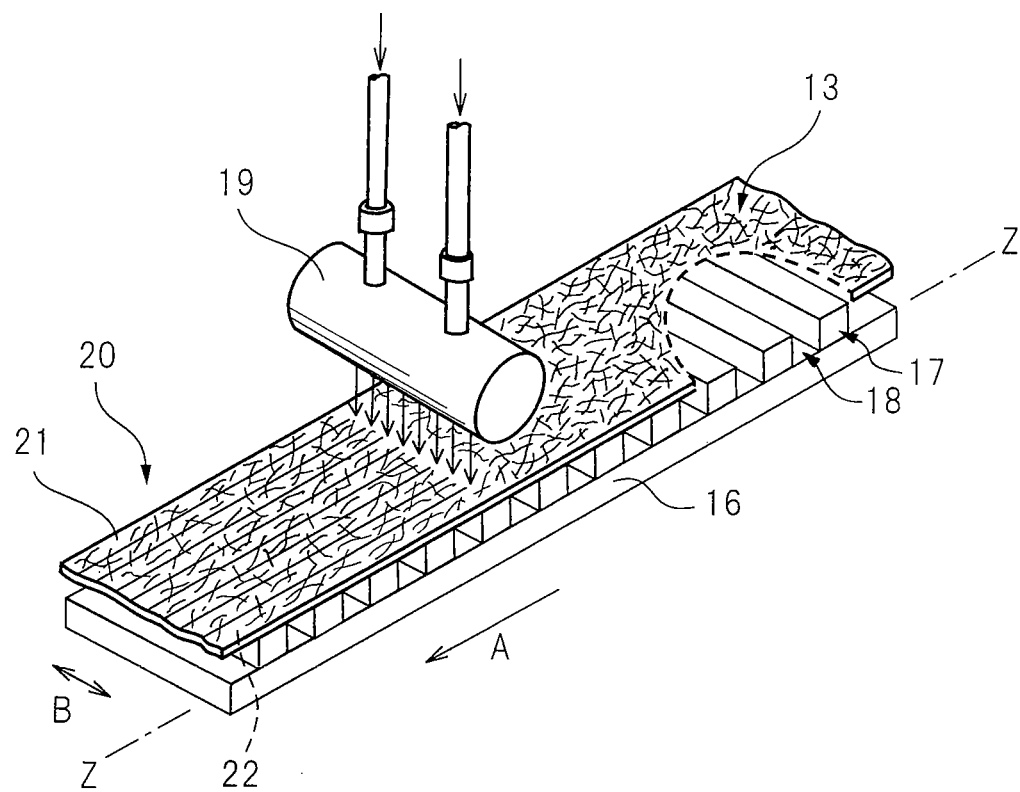
FIG. 7 is a diagram showing an example of a fluid treatment step.

FIG. 7 is a diagram showing an example of a fluid treatment step using a support. The support 16 shown in FIG. 7 has protrusions 17 and depressions 18 running parallel in the cross direction B, and the protrusions 17 and depressions 18 are arranged in an alternating fashion in the machine direction A. In the support 16 shown in FIG. 7, the protrusions 17 and depressions 18 have cubic shapes.

A fluid nozzle 19 is also shown in FIG. 7, and below the fluid nozzle 19 there is provided a suction section (not shown) that receives fluid, sandwiching the support 16.

A fluid is blasted from the fluid nozzle 19 onto a nonwoven fabric 13 having high-stretch regions and low-stretch regions that has been placed on a support 16 and carried in, thus forming a nonwoven fabric 20 having a specific tangled and/or fused structure. The blasted fluid is discharged from the suction section (not shown).

In FIG. 7, the side of the nonwoven fabric 20 with a specific tangled and/or fused structure onto which the fluid has been blasted is the first side 21, while the surface of the support 16 side is the second side 22.

Also, the support 16 shown in FIG. 7 has the protrusions 17 and depressions 18 arranged parallel to the cross direction and alternating in the machine direction, but there are no particular restrictions on the shapes and arrangement of the protrusions and depressions for the method of forming a nonwoven fabric of the invention, and for example, the protrusions and depressions: (i) may be protrusions and depressions that are all parallel to the machine direction and alternatingly disposed in the cross direction, (ii) may be protrusions and depressions that are slanted with respect to the machine direction and alternatingly disposed in the direction perpendicular to the slanted direction, or (iii) protrusions and/or depressions having predetermined shapes (for example, cubic, cylindrical or hemispherical) may be disposed in a predetermined arrangement (for example, a heart-shaped or star-shaped arrangement).

Figure 8:
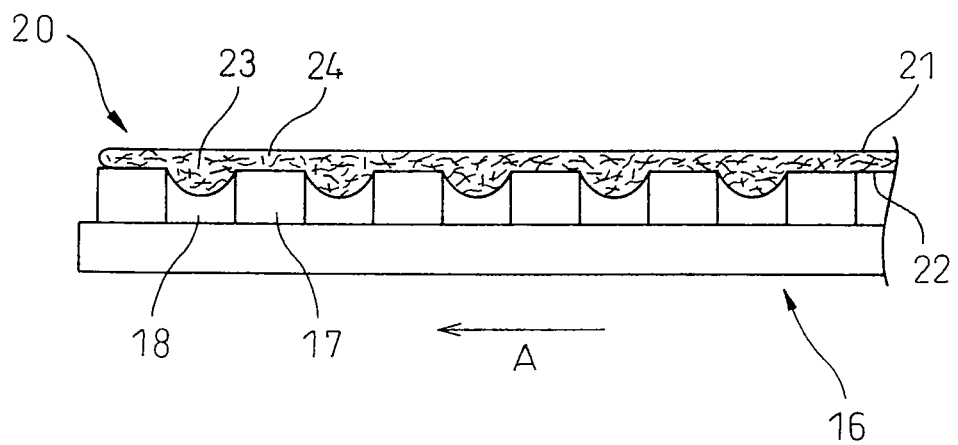
FIG. 8 is a diagram illustrating a nonwoven fabric having a specific tangled and/or fused structure formed using the support shown in FIG. 7.

This phenomenon will be concretely described with reference to FIG. 7 and FIG. 8. FIG. 8 is a diagram showing a nonwoven fabric 20 having a specific tangled and/or fused structure formed using the support 16 shown in FIG. 7, and it corresponds to a cross-section along line Z-Z in FIG. 7.

When the fluid blasted from the fluid nozzle 19 impacts protrusions 17, it flows into and around the depressions 18. As a result, the extended composite fibers that have a high degree of freedom move with the fluid flow toward the depressions 18, such that the amount of composite fiber per unit area is reduced at the locations where the fluid and the protrusions 17 cross, forming recesses 24 in the nonwoven fabric having high-stretch regions and low-stretch regions and in some cases forming one or more open holes, while the amount of composite fiber per unit area is increased at the locations where the fluid and the depressions 18 cross, forming projections 23 in the nonwoven fabric having high-stretch regions and low-stretch regions. In the nonwoven fabric 20 with a specific tangled and/or fused structure, shown in FIG. 7 and FIG. 8, the side onto which the fluid has been blasted is the first side 21, while the surface of the support 16 side is the second side 22.

Since the extended composite fibers tend to rise in the thickness direction of the nonwoven fabric at the projections 23, the nonwoven fabric is imparted with compression resistance and liquid permeability. Also, the presence of the projections 23 and recesses 24 results in satisfactory air permeability of the nonwoven fabric, and especially air permeability in the planar directions, while the contact area is also reduced so that the feel of the nonwoven fabric on the skin is satisfactory.

Of the air permeability in the planar directions, the nonwoven fabric formed using the support shown in FIG. 7 has particularly excellent air permeability in the cross direction. This is because the recesses 24 of the nonwoven fabric corresponding to the protrusions of the support can serve as gas channels.

When a support is used for a nonwoven fabric formed by the method of forming a nonwoven fabric according to the invention, the diameters of the composite fibers at the projections on the second side will sometimes be smaller than the diameters of the composite fibers at the recesses on the second side. For example, when the fluid treatment step has been carried out using a support as illustrated in FIG. 7, the composite fibers that have been extended to small diameters and long lengths in the non-homogeneous stretching step move from the locations corresponding to the recesses on the second side toward the direction of the protrusions 17, thus tending to form projections 23 on the second side.

The diameters of the composite fibers can be determined by randomly picking up fibers within a prescribed area of an image photographed with an electron microscope or the like, measuring the diameters at a fixed number of locations, such as 50, on the image, and calculating the arithmetic mean.

When a support is used, the nonwoven fabric formed by the method of the invention will sometimes have a percentage of detached portions at the projections on the second side that is higher than the percentage of detached portions at the recesses on the second side. For example, when the fluid treatment step has been carried out using a support as illustrated in FIG. 7, the detached portions formed in the non-homogeneous stretching step move from the locations corresponding to the recesses on the second side toward the direction of the protrusions 17, thus tending to form projections 23 on the second side.

The percentage of detached portions may be determined, for example, by counting the number of detached portions within a prescribed area of an image photographed with an electron microscope or the like.

In the support, the protrusions preferably have lower fluid permeability than the fluid permeability of the depressions. This is because with low fluid permeability at the protrusions, the fluid impacting the protrusions will flow toward the depressions, thus allowing formation of greater projections in the nonwoven fabric formed by the method of forming a nonwoven fabric of the invention.

The material of the protrusions may be metal, plastic or other suitably strong material.

The shapes and materials of the protrusions and depressions are not particularly restricted, and the support may be formed by situating cubic or tubular-shaped metal in a predetermined arrangement, maintaining a fixed spacing, for example, on a metal or plastic conveyor net, paper-making net or punching plate that is commonly used as a fluid-permeable support.

Examples of supports having protrusions and/or depressions with predetermined shapes (for example, cubic, cylindrical or hemispherical) arranged in a predetermined form (for example, heart-shaped or star-shaped) include supports having hemispherical metal situated in a predetermined arrangement (such as a heart-shaped arrangement) on a punching plate. When such a support is used, it is possible to form a nonwoven fabric having recesses in a predetermined pattern (for example, heart-shaped).

Also, by using a support with protrusions and depressions, in which hemispherical dent shapes are arranged in a predetermined pattern (such as a heart-shaped pattern) on a punching plate, it is possible to form a nonwoven fabric having projections in a predetermined pattern (such as a heart-shaped pattern).

The punching plate itself may also be used as the support. Examples of punching plates that may be used as supports include round hole-type punching plates, such as round hole 60° zigzag types, round hole square zigzag types and round hole serial types, ratchet types, round cross types, cloud types, and cloud zigzag types. When a punching plate is used as the support, the plate sections serve as the protrusions and the open sections serve as the depressions.

By selecting the shape of the support for the method of forming a nonwoven fabric of the invention, it is possible to impart a desired pattern, desired air permeability and desired flexibility to the nonwoven fabric before non-homogeneous stretching, and thus accomplish easy and inexpensive modification of commercially available nonwoven fabrics according to desired purposes.

When the fluid treatment step is to be carried out on a roll, a roll-like support may be used, having the outer periphery constructed of a fluid-permeable material such as a mesh and having protrusions and depressions situated with predetermined shapes and a predetermined arrangement, on the peripheral surface. The predetermined shapes and arrangement may be the shapes and arrangement described above.

In a support having protrusions and depressions, their widths will differ depending on the shape to be formed and on the properties required for the nonwoven fabric having a specific tangled and/or fused structure, but as an example, the support shown in FIG. 7 preferably has protrusion widths in the range of about 0.5 to about 10 mm, and depression widths in the range of about 1 to about 10 mm.

A nonwoven fabric having a first side with a plurality of projections and a plurality of recesses, and/or a second side having a plurality of projections and a recess, has a small contact area with the skin and can therefore reduce the feeling of stickiness caused by mustiness resulting from a large contact area, as well as the feeling of irritation caused by rubbing, and it is therefore suitable for purposes such as absorbent articles.

Incidentally, when the nonwoven fabric of the invention has a first side with a plurality of projections and a plurality of recesses and a second side with a plurality of projections and a recess, the side with the larger difference of elevation between the projections and recesses is preferably used as the side in contact with the body, in order to further reduce contact area with the skin.

A nonwoven fabric of the invention or a nonwoven fabric formed by the method of the invention is useful for absorbent articles such as sanitary products and disposable diapers, cleaning products such as wipers, and medical goods such as masks.

A nonwoven fabric formed by the method described above can be used as a liquid-permeable top sheet for an absorbent article, for example. By using a nonwoven fabric that is flexible, has excellent feel on the skin, exhibits high air permeability and liquid permeability, has high deformability and has excellent recoverability, it is possible to produce absorbent articles having the same superior qualities.

Such an absorbent article may comprise a nonwoven fabric of the invention as the liquid-permeable top sheet, a liquid-impermeable back sheet, and an absorbent core between the liquid-permeable top sheet and the liquid-impermeable back sheet.

EXAMPLES

The invention will now be explained in greater detail using examples and comparative examples, with the understanding that the invention is in no way limited by the examples.

The evaluated properties and measuring conditions in the examples and comparative examples were as follows.

[Basis Weight]

The basis weight was measured according to JIS L 1906, 5.2.

[Bulk]

The bulk was measured using a THICKNESS GAUGE UF-60 by Daiei Kagaku Seiki Mfg. Co., Ltd.

[Strength and Ductility]

The strength and ductility were measured using a Model AG-KNI autograph tensile tester by Shimadzu Corp.

A sample with a 50 mm width was anchored to a chuck with a chuck distance of 100 mm, and extended at a pull rate of 100 mm/min. The strength at 5%, or 5 mm extension, was recorded as the "5% strength", the strength at 50%, or 50 mm extension was recorded as the "50% strength" and the maximum of the strength obtained during extension was recorded as the "maximum point strength" while the ductility at that point was recorded as the "maximum point ductility".

"MD" in the table indicates the machine direction during formation of the nonwoven fabric, and "CD" indicates the cross direction during formation of the nonwoven fabric.

[Compression Property]

The compression property was evaluated using a KES-FB3 automated compression tester by Kato Tech Corp.

The measuring conditions were as follows.
SENS: 2
Speed: 0.02 mm/sec
Stroke: 5 mm/10 V
Compression area: 2 cm$^2$
Uptake interval: 0.1 second
Load limit: 50 g/cm$^2$
Repeat frequency: 1

The compression property was evaluated based on the compressional work WC and the compressional resilience RC, per 1 cm$^2$ of nonwoven fabric. A larger WC value indicates greater ease of compression, while an RC closer to 100% indicates higher recoverability.

[Air Permeability]

The air permeability was measured using a KES-F8-AP1 air permeability tester by Kato Tech Corp., with calculation in units of m$^3$/m$^2$/min.

The air permeability in the thickness direction of the nonwoven fabric was measured by setting the nonwoven fabric, cut to a size of 100 mm×100 mm, in the air permeability tester.

The air permeability in the planar direction of the nonwoven fabric was measured with the nonwoven fabric cut to a size of 100 mm×100 mm and set in the air permeability tester, a 100 mm×100 mm acrylic board set thereover and application of a pressure of 3.5 mN/cm$^2$.

[Liquid Permeability]

The liquid permeability was evaluated using a LISTER strikethrough tester by Lenzing AG. The evaluation procedure was as follows.

(1) The sample cut to a size of 100×100 mm was placed on 5 sheets of filter paper (Advantec Filter Paper Grade 2) cut to sizes of 100×100 mm, and an electrical liquid permeation plate was placed thereover.

(2) The filter paper, sample and electrical liquid permeation plate were set on the strikethrough tester.

(3) A 5 mL portion of physiological saline was poured into the strikethrough tester.

(4) The physiological saline (room temperature) was allowed to drop from the strikethrough tester through an open hole in the electrical liquid permeation plate.

(5) The electrification time of the electrical liquid permeation plate was recorded.

(6) The measurement was repeated twice and the average value for the total of 3 times was recorded as the liquid permeation time.

When no sample was set, i.e. with only 5 filter paper sheets, the liquid permeation time was 69 seconds.

Example 1

Preparation of Nonwoven Fabric

A commercially available air-through nonwoven fabric was prepared. The air-through nonwoven fabric was formed from 100 mass % core-sheath composite fibers having a core of polyethylene terephthalate with a melting point of approximately 250° C. and a sheath of polyethylene with a melting point of approximately 130° C.

Figure 9:
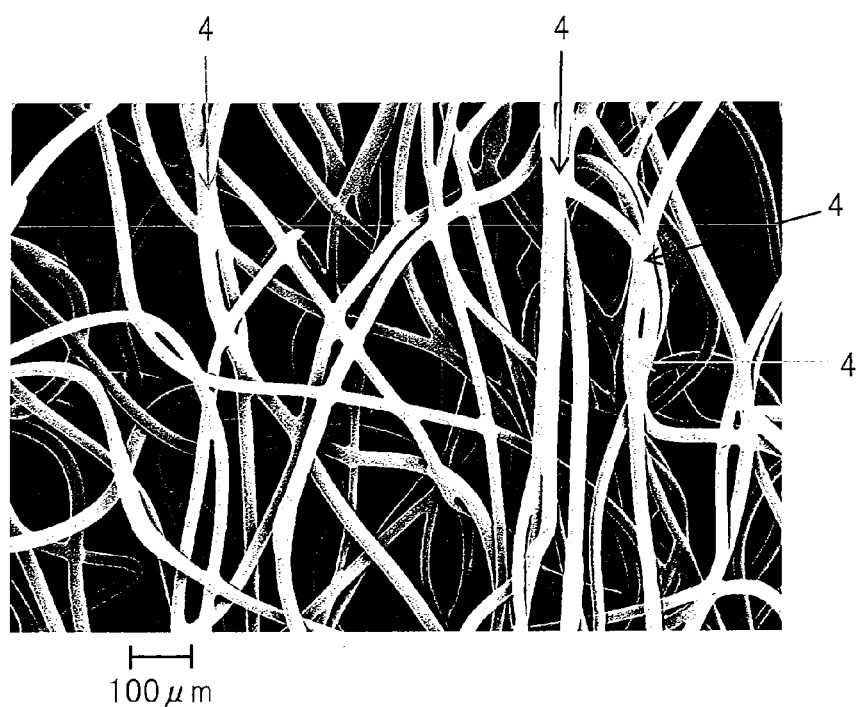
FIG. 9 is a scanning electron micrograph of the air-through nonwoven fabric used in Examples 1-4 and Comparative Example 1.

The property values of the air-through nonwoven fabric are shown in Table 1. A scanning electron micrograph of the surface of the air-through nonwoven fabric is shown in FIG. 9. From FIG. 9 it is seen that the air-through nonwoven fabric had many joining sections 4 between composite fibers, and an even greater bonding area.

—Gear Stretching—

The air-through nonwoven fabric was subjected to gear stretching using a gear stretcher such as shown in FIG. 5 (gear pitch: 2.5 mm, gear tip width: 0.2 mm, gear tooth cutting depth: 4.0 mm), to form a nonwoven fabric having high-stretch regions and low-stretch regions. The throughput was 30 m/min. The draw ratio of the nonwoven fabric having high-stretch regions and low-stretch regions was 235%.

Figure 10:
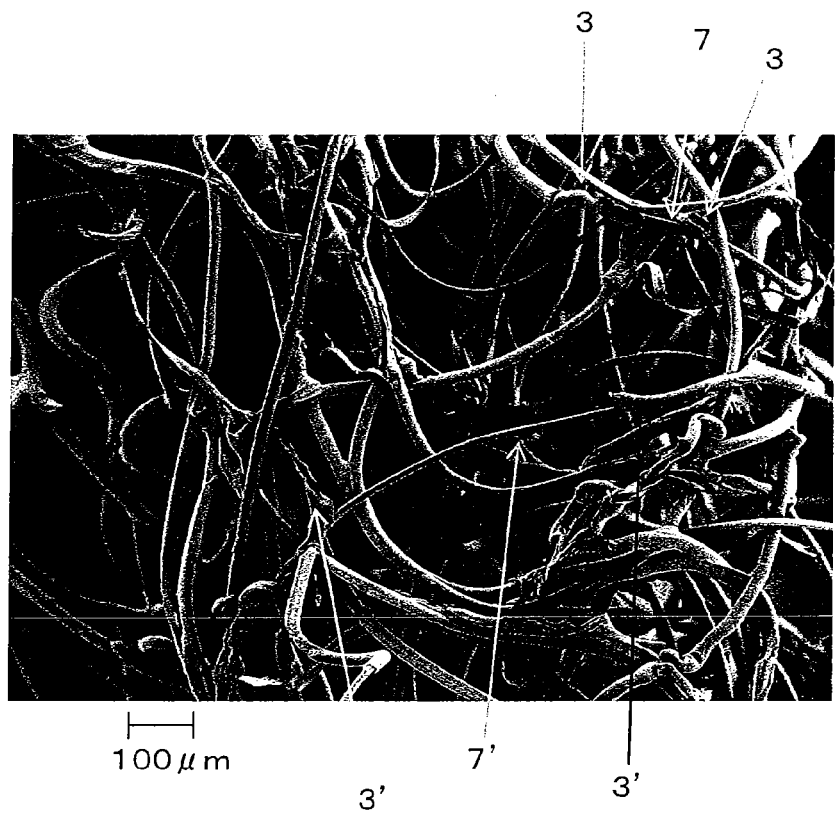
FIG. 10 is a scanning electron micrograph of a nonwoven fabric having a high-stretch region and a low-stretch region, produced in Example 1.

The property values of the nonwoven fabric having high-stretch regions and low-stretch regions are shown in Table 1. FIG. 10 shows a scanning electron micrograph of the surface of the nonwoven fabric having high-stretch regions and low-stretch regions. In FIG. 10, there can be seen detached portions 3 and 3' consisting of the second component and exposed portions 7 and 7' of the first component that are not covered by the second component.

—Steam Treatment—

The nonwoven fabric having high-stretch regions and low-stretch regions was placed on a mesh-like support with a thickness of 1.0 mm. The support was formed from heat-resistant polyethylene terephthalate wire with a diameter of 0.6 mm, with 22 wires per inch. Next, the nonwoven fabric having high-stretch regions and low-stretch regions was passed through a steam treatment system comprising a plurality of nozzles (φ: 0.5 mm) at 1.0 mm spacings (spray pressure: 0.5 Mpa, water vapor temperature: 149° C.), at a speed of 30 m/min while maintaining a distance of 5.0 mm between the nozzles and support, to obtain a nonwoven fabric 1.

The property values of the nonwoven fabric 1 are shown in Table 1. Scanning electron micrographs of the cross-section and surface of the nonwoven fabric 1 are shown in FIG. 11 and FIG. 12.

Figure 11:
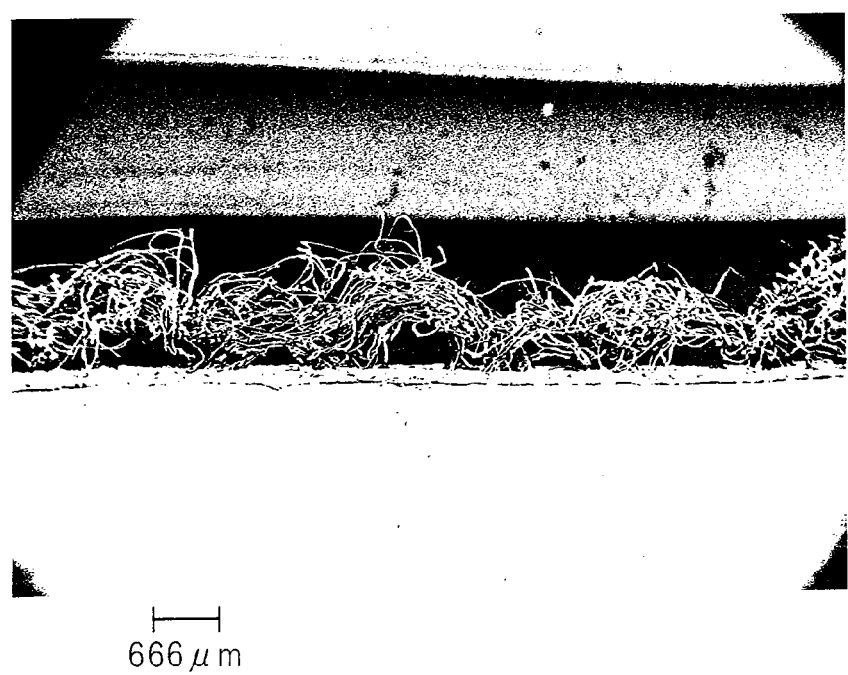
FIG. 11 is a scanning electron micrograph of the cross-section of the nonwoven fabric 1 formed in Example 1.

In the nonwoven fabric 1 shown in FIG. 11, the top side is the first side on the steam treatment side while the bottom side is the second side on the support side, with the left-right directions corresponding to the cross direction.

Figure 12:
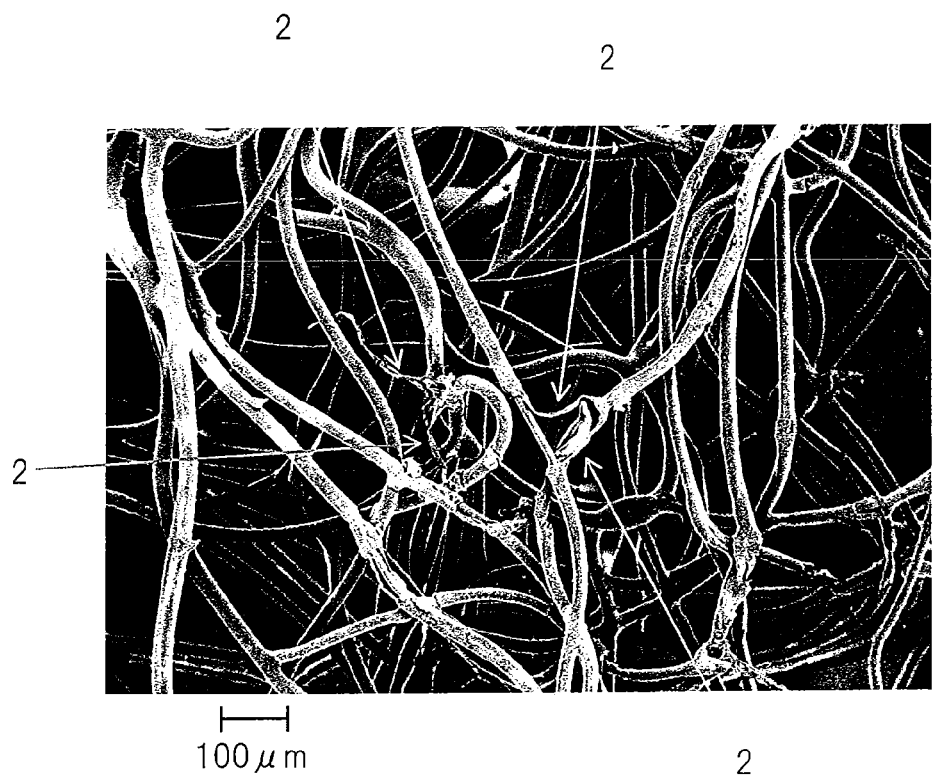
FIG. 12 is a scanning electron micrograph of the surface of the nonwoven fabric 1 formed in Example 1.

FIG. 12 shows that the nonwoven fabric 1 has a plurality of detached portions 2 tangled and/or fused with other composite fibers.

Example 2

A nonwoven fabric 2 was obtained in the same manner as Example 1, except that the support was changed to a round hole 60° zigzag-type punching plate (φ: 3.0 mm, MD pitch: 6.94 mm, CD pitch: 4.0 mm, thickness: 1.0 mm), and a distance of 4.0 mm was maintained between the nozzles and support.

The property values of the nonwoven fabric 2 are shown in Table 1.

Example 3

A nonwoven fabric 3 was obtained in the same manner as Example 2, except that the spray pressure was changed to 0.3 Mpa and the water vapor temperature was changed to 131° C.

The property values of the nonwoven fabric 3 are shown in Table 1.

Example 4

A nonwoven fabric 4 was obtained in the same manner as Example 2, except that the spray pressure was changed to 0.2 Mpa and the water vapor temperature was changed to 119° C.

The property values of the nonwoven fabric 4 are shown in Table 1.

Comparative Example 1

A nonwoven fabric 5 was obtained in the same manner as Example 2, except that no gear stretching was carried out and the steam treatment was repeated twice.

Figure 13:
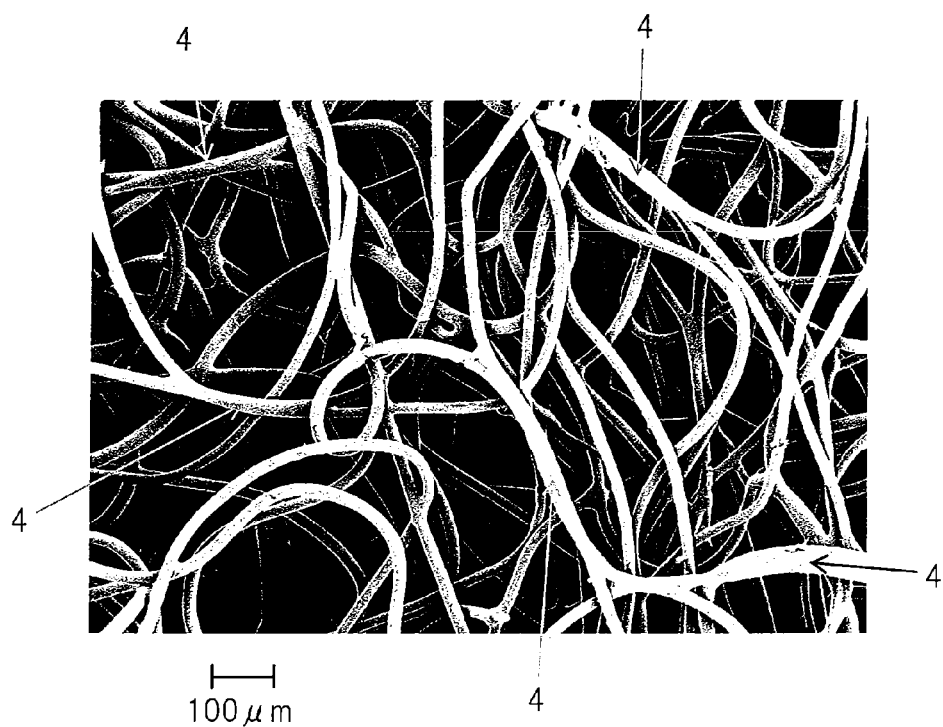
FIG. 13 is a scanning electron micrograph of the surface of the nonwoven fabric 5 formed in Comparative Example 1.

The property values of the nonwoven fabric 5 are shown in Table 1. A scanning electron micrograph of the surface of the nonwoven fabric 5 is shown in FIG. 13. FIG. 13 shows that the nonwoven fabric 5 of Comparative Example 1 had numerous joining sections 4 and a large bonding surface area.

Comparative Example 1 corresponds to the nonwoven fabric described in PTL 1.

TABLE 1

| | | Example 1 | Example 2 | Example 3 | Example 4 | Comp. Example 1 |
|---|---|---|---|---|---|---|
| | | Nonwoven fabric 1 | Nonwoven fabric 2 | Nonwoven fabric 3 | Nonwoven fabric 4 | Nonwoven fabric 5 |
| Original properties | | | | | | |
| Basis weight | g/m² | | | 20.5 | | |
| Bulk | mm | | | 0.28 | | |
| Strength and ductility (machine direction) | 5% strength (N) | | | 8.1 | | |
| | Max. point strength (N) | | | 34.2 | | |
| | Max. point ductility (%) | | | 42.7 | | |
| Strength and ductility (cross direction) | 50% strength (N) | | | 3.3 | | |
| | Max. point strength (N) | | | 6.6 | | |
| | Max. point ductility (%) | | | 108 | | |
| Compression properties | WC(N·m/m²) | | | 0.2 | | |
| | RC(%) | | | 58 | | |
| Air permeability (thickness direction) | m³/m²/min | | | 960 | | |
| Air permeability (planar direction) | m³/m²/min | | | 2 | | |
| Liquid permeability | Liquid permeation time (sec) | | | 37 | | |
| Properties after gear stretching | | | | | | |
| Basis weight | g/m² | | | 14.9 | | |
| Bulk | mm | | | 0.49 | | |
| Strength and ductility (machine direction) | 5% strength (N) | | | 1.8 | | |
| | Max. point strength (N) | | | 18.0 | | |
| | Max. point ductility (%) | | | 45.4 | | |
| Strength and ductility (cross direction) | 50% strength (N) | | | 0.0 | | |
| | Max. point strength (N) | | | 4.8 | | |
| | Max. point ductility (%) | | | 144 | | |
| Steam treatment conditions | | | | | | |
| Steam pressure | Mpa | 0.5 | 0.5 | 0.3 | 0.2 | 0.5 |
| Steam temperature | °C. | 149 | 149 | 131 | 119 | 149 |
| Treatment frequency | Number of times | 1 | 1 | 1 | 1 | 2 |

TABLE 1-continued

| | | Example 1 | Example 2 | Example 3 | Example 4 | Comp. Example 1 |
|---|---|---|---|---|---|---|
| | | Nonwoven fabric 1 | Nonwoven fabric 2 | Nonwoven fabric 3 | Nonwoven fabric 4 | Nonwoven fabric 5 |
| Properties after steam treatment | | | | | | |
| Basis weight | g/m² | 16.9 | 15.2 | 13.9 | 14.4 | 21.4 |
| Bulk | mm | 0.60 | 0.55 | 0.46 | 0.44 | 0.68 |
| Strength and ductility (machine direction) | 5% strength (N) | 1.9 | 0.5 | 0.8 | 0.6 | 5.1 |
| | Max. point strength (N) | 20.3 | 15.3 | 16.4 | 16.1 | 33.1 |
| | Max. point ductility (%) | 46.1 | 45.2 | 46.0 | 47.8 | 43.5 |
| Strength and ductility (cross direction) | 50% strength (N) | 0.1 | 0.2 | 0.1 | 0.1 | 3.6 |
| | Max. point strength (N) | 4.6 | 4.2 | 4.0 | 4.0 | 6.7 |
| | Max. point ductility (%) | 142 | 129 | 125 | 114 | 110 |
| Compression properties | WC(N·m/m²) | 0.8 | 0.8 | 0.7 | 0.7 | 0.6 |
| | RC(%) | 32 | 40 | 39 | 38 | 44 |
| Air permeability (thickness direction) | m³/m²/min | 1700 | 2340 | 2410 | 2140 | 910 |
| Air permeability (planar direction) | m³/m²/min | 12 | 19 | 13 | 11 | 20 |
| Liquid permeability | Liquid permeation time (sec) | 33 | 45 | 15 | 18 | 60 |

The nonwoven fabrics 1-4 formed in Examples 1-4 had MD 5% strengths of 0.6-1.9N and CD 50% strengths of 0.1-0.2N. These values were smaller than the MD 5% strengths and CD 50% strengths of the original air-through nonwoven fabrics and the nonwoven fabric of Comparative Example 1. The same tendency was also seen for the MD and CD maximum point strengths. This suggested that the nonwoven fabrics 1-4 formed in Examples 1-4 were flexible and had satisfactory feel on the skin.

The nonwoven fabrics 1-4 formed in Examples 1-4 also had WC values of 0.7-0.8 N·m/m² and RC values of 32-40%. Thus, the nonwoven fabrics 1-4 had higher deformability and equivalent recoverability compared to the nonwoven fabric 5 of Comparative Example 1 (WC: 0.6 N·m/m², RC: 44%).

Moreover, the nonwoven fabrics 1-4 formed in Examples 1-4 had air permeabilities (in the thickness direction) of 1700-2410 m³/m²/min and air permeabilities (in the planar direction) of 11-19 m³/m²/min, and thus exhibited excellent air permeability.

In addition, the nonwoven fabrics 1-4 formed in Examples 1-4 had liquid permeabilities of 15-33 seconds, which was superior liquid permeability to that of the nonwoven fabric of Comparative Example 1 (liquid permeability: 60 sec).

Since the nonwoven fabrics 1-4 formed in Examples 1-4 did not have highly dense sections, unlike the nonwoven fabric 5 of Comparative Example 1, their air permeabilities and liquid permeabilities were attributed to lack of inhibition of aeration so that absorbed liquids were not continuously retained.

REFERENCES SIGNS LIST 1,1' Composite fibers
2 Detached portion tangled and/or fused with other composite fiber
2' Detached portion not tangled and/or fused with other composite fiber
3 Detached portion
4 Joining section
5 First component
6 Second component
7,7' Exposed portions
8 Gear stretcher
9,9' Gear rolls
10,10' Peripheral surfaces
11,11' Teeth
12 Nonwoven fabric comprising composite fibers including a first component and second component having a lower melting point than the first component
13 Nonwoven fabric having high-stretch regions and low-stretch regions
14 Gear pitch
15 Gear tooth cutting depth
16 Support
17 Protrusion
18 Depression
19 Fluid nozzle
20 Nonwoven fabric with specific tangled and/or fused structure
21 First side
22 Second side
23 Projection
24 Recess
A Machine direction
B Cross direction perpendicular to machine direction
E High-stretch region

The invention claimed is:

1. A nonwoven fabric comprising composite fibers that include a first component and a second component having a lower melting point than the first component,
wherein the nonwoven fabric has high-stretch regions and low-stretch regions,
wherein the nonwoven fabric is formed by non-homogeneous stretching of a nonwoven fabric comprising composite fibers that include a first component and a second component having a lower melting point than the first component so as to form the high-stretch and low-stretch regions, and wherein the composite fibers have detached portions created by the non-homogeneous stretching to detach at least a portion of the second component from the first component and/or residual portions of the second component, and at least some of the detached portions are tangled and/or fused with other composite fibers.

2. The nonwoven fabric according to claim 1, wherein the detached portions are created by detaching at least a portion of the second component from the first component and/or the residual portions of the second component along roughly the longitudinal axial direction of the composite fibers.

3. The nonwoven fabric according to claim 1, wherein the composite fibers are selected from the group consisting of core-sheath composite fibers, sea-island composite fibers, split mold composite fibers, side-by-side composite fibers and mixtures thereof.

4. The nonwoven fabric according to claim 1, wherein the composite fibers are core-sheath composite fibers in which the first component is the core and the second component is the sheath, and a portion of the core is exposed without being covered by the sheath.

5. The nonwoven fabric according to claim 1, wherein the nonwoven fabric has a first side with a plurality of projections and a plurality of recesses, and a second side on the opposite side from the first side, with a plurality of projections and a recess.

6. The nonwoven fabric according to claim 5, wherein the diameter of the composite fibers in the projections of the second side is smaller than the diameter of the composite fibers in the recesses on the second side.

7. The nonwoven fabric according to claim 5, wherein the percentage of the detached portions among the projections on the second side is higher than the percentage of the detached portions among the recesses on the second side.

8. The nonwoven fabric according to claim 1, wherein the first component has a melting point of at least 20° C. higher than the melting point of the second component.

9. The nonwoven fabric according to claim 1, wherein the nonwoven fabric is formed by non-homogeneous stretching of an air-through nonwoven fabric comprising composite fibers comprising the first component, and the second component having a lower melting point than the first component, so that a nonwoven fabric with high-stretch regions and low-stretch regions is formed, followed by spraying a fluid onto the nonwoven fabric with high-stretch regions and low-stretch regions.

10. An absorbent article comprising a liquid-permeable top sheet, a liquid-impermeable back sheet and an absorbent core between the liquid-permeable top sheet and liquid-impermeable back sheet,
wherein the liquid-permeable top sheet is the nonwoven fabric according to claim 1.

11. A method of forming the nonwoven fabric according to claim 1, comprising the steps of,
providing a nonwoven fabric comprising
composite fibers comprising a first component, and a second component having a lower melting point than the first component,
non-homogeneous stretching of the nonwoven fabric comprising the composite fibers comprising the first component and the second component having a lower melting point than the first component, so that detached portions are created by detaching at least a portion of the second component from the first component and/or residual portions of the second component, to form a nonwoven fabric with high-stretch regions and low-stretch regions, and
spraying a fluid onto the nonwoven fabric with high-stretch regions and low-stretch regions so that at least some of the detached portions are tangled and/or fused with other composite fibers, to form the nonwoven fabric according to claim 1.

12. The method according to claim 11, wherein in the step of spraying the fluid, a support having protrusions and depressions with predetermined shapes and arrangements is placed on the side opposite the fluid-sprayed side of the nonwoven fabric with high-stretch regions and low-stretch regions.

13. The method according to claim 11, wherein the fluid is heated air, saturated steam or superheated steam.

14. The method according to claim 11, wherein the nonwoven fabric comprising composite fibers comprising the first component and the second component having a lower melting point than the first component are of an air-through nonwoven fabric.

\* \* \* \* \*